United States Patent [19]
Maslak et al.

[11] Patent Number: 5,148,810
[45] Date of Patent: Sep. 22, 1992

[54] VARIABLE ORIGIN-VARIABLE ANGLE ACOUSTIC SCANNING METHOD AND APPARATUS

[75] Inventors: Samuel H. Maslak, Redwood City; Hugh G. Larsen, Palo Alto; Joel S. Chaffin, Saratoga; Paul E. Chandler, Santa Cruz; Ian A. Galton, Pasadena; Mehebub S. Karmali, Fremont, all of Calif.

[73] Assignee: Acuson Corporation, Mountain View, Calif.

[21] Appl. No.: 552,019

[22] Filed: Jul. 13, 1990

Related U.S. Application Data

[63] Continuation-in-part of Ser. No. 478,573, Feb. 12, 1990.

[51] Int. Cl.$^5$ ............................................. A61B 8/00
[52] U.S. Cl. ..................... 128/661.01; 128/660.01; 73/597
[58] Field of Search ................ 128/660.01, 661.01; 73/625–626

[56] References Cited

U.S. PATENT DOCUMENTS

| | | | |
|---|---|---|---|
| 4,159,462 | 6/1979 | Rocha et al. | 73/626 X |
| 4,344,327 | 8/1982 | Yoshikawa et al. | 73/626 |
| 4,368,643 | 1/1983 | Tachita et al. | 73/626 |
| 4,440,025 | 4/1984 | Hayakawa et al. | 73/626 X |
| 4,550,607 | 11/1985 | Maslak et al. | 73/626 |
| 4,569,231 | 2/1986 | Carnes et al. | 73/626 |
| 4,638,467 | 1/1987 | Takeuchi | 73/626 X |
| 4,915,115 | 4/1990 | Sasaki et al. | 128/660.05 |

Primary Examiner—Francis Jaworski
Attorney, Agent, or Firm—James F. Mitchell

[57] ABSTRACT

An acoustic scanning method and apparatus implemented by transmitting ultrasonic pressure waves and receiving return echoes on a set of spatially non-overlapping acoustic lines scanned along a transducer array with the active acoustic lines shifted and steered so that each acoustic line originates at an arbitrary point on and at an arbitrary angle to the face of the array. In a preferred embodiment, an extension of each acoustic line may also pass through a substantially common vertex that is not on the face of the transducer array, but preferably behind it a selectable distance to provide an extended field of view. The extended field-of-view is defined by the selectively variable location of the common vertex of the acoustic lines and the physical ends of the array, may use the entire transducer array in the near-field, has high quality resolution in both near and far fields, and may simultaneously transmit and receive two or more ultrasound beams from the same transducer aperture.

21 Claims, 12 Drawing Sheets

VARIABLE ORIGIN-VARIABLE ANGLE ACOUSTIC SCANNING METHOD AND APPARATUS

This application is a continuation-in-part of application Ser. No. 478,573 filed Feb. 12, 1990.

BACKGROUND OF THE INVENTION

This invention relates to ultrasound diagnostic scanning where ultrasonic energy illuminates internal organs of the human body in real time and echoes received from the soft organ tissues or from moving scatterers are transduced into electrical signals and then processed to form two-dimensional cross-sectional images that are displayed upon a TV monitor or like display device.

Ultrasound medical systems known as phased arrays have been used for some time and have been described, for example, in U.S. Pat. Nos. 4,140,022 and 4,550,607. Two basic scan and display formats have generally been used in combination with planar linear transducer arrays, that is arrays in which the face of individual transducer elements are positioned in a plane parallel to each other and generally have uniform element spacing.

Two-dimensional images have been formed by linear scanning where ultrasonic beams on parallel acoustic lines normal to or at an angle to the face of a transducer array are propagated by single transducer elements or by selected groups of transducer elements shifted across the array. Linear scanning with parallel lines has the field of view determined by the physical aperture of the transducer array 1 such as width W in FIG. 1. For such a format, the width of the field of view 5 (FOV) is equal to the transducer width W for all scan depths D. Thus, the field of view in the linear scanning format is defined completely by the physical characteristics of the array and is limited by the physical edge of the array. A large field of view requires a large physical aperture of active transducer elements which may create problems of access and good skin contact.

The other scan and display format which is typically used for planar linear transducer arrays is a sector. In a sector format, the elements are spaced much closer together, typically at half-wavelength or so intervals. This permits the acoustic scan lines to be steered without generating grating lobes and allows both the size of the transducer array to be decreased and the field of view to be increased. For example, as shown in FIG. 2, for a 90° sector, the field of view 2 at a scan depth D is given by FOV=2D. Typical scan depths range from 6 cm to 24 cm and are user selectable. Sector phased arrays form acoustic scan lines effectively all originating from the center of the face of the transducer array. The allowable scan angle is a function of the spacing of the individual transducer elements relative to operating frequency. As a consequence, the field of view is also largely defined by the physical characteristics of the array and the field of view vanishes to zero at the face of the array, itself A "trapezoidal" scanning and display format has been described in U.S. Pat. No. 4,664,122, which is specific to a particular planar linear array construction. It consists of three sub-arrays, including a central sub-array with substantially larger element spacing, and two end sub-arrays with substantially smaller element spacing. There is a fixed relationship between the element spacing of the central sub-array compared to the end sub-array such as a factor of 2. Acoustic scan lines emanating from the central sub-array and from portions of the two end sub-arrays are parallel to each other, are perpendicular to the transducer face, and are consistent with a linear scan format. Acoustic scan lines emanating from a single point on the face of each end sub-array comprise a left-half and right-half sector. The described end sub-arrays have smaller element spacing, approximately one-half of the transducer wavelength, in order to permit steering the acoustic beams out to angles of approximately 45° with acceptable performance.

Since most transducers which are designed for medical ultrasound imaging systems have uniform element spacing, this "trapezoidal" scanning technique is not advantageous because it does require special transducers with non-uniform element spacing. Transducers which are specifically designed for this format are typically larger than those designed for "sector" scanning. The trapezoidal scan format is described as a compromise between linear and sector scanning, having the advantage of steering, but with the disadvantage of increased transducer size. This size disadvantage is inherent because the increase in the field of view of the displayed image compared to a sector image is increased only to the extent that the transducer is increased in size over that for a corresponding sector transducer. The scan format also is specifically linked to the transducer array construction in contrast to the invention disclosed herein where the scan format is alterable under software control in order to optimize it for different imaging applications using the same transducer geometry.

The physical characteristics of curvilinear arrays also define a field of view which is limited by acoustic lines normal to the face of the array at the end transducer elements. The field of view can be increased by a smaller radius of curvature. However, resolution is impaired and thereby degraded as compared to a less curved array. Also, a large field of view in the nearfield requires a large aperture of active transducer elements. A large field of view in the far-field requires some combination of a large aperture and/or a smaller radius of curvature with the attendant loss of resolution.

All the foregoing formats, as well as mechanical and waterpath scanning, have the field of view defined completely by the physical characteristics of the array. In none of these prior art scanning formats is the field of view expanded by situation-dependent software control.

SUMMARY OF THE INVENTION

The acoustic scanning method of this invention involves the propagation of acoustic pressure waves and the reception of returned echoes on a set of acoustic scan lines which are formed by software control, each independent from one another, each originating at an arbitrary point on the face of the transducer array and at an arbitrary angle to the face of the array which may have virtually any configuration. In a preferred embodiment, each scan line may also be part of a ray which passes through a substantially common variably located vertex that is typically not on the face of the transducer array, but preferably a selectable distance behind it to provide an extended field of view. In the embodiments described in detail, for convenience called variable vertex scanning, the transducer arrays are planar linear or curvilinear arrays. If the latter, the common vertex is behind the curvilinear face of the array a distance typically less than the radius of curvature of the array. The acoustic lines thus can be steered beyond both ends of the array itself, to extend the field of view at all depths with substantially comparable resolution.

The described embodiments improve the field of view without increasing the size of the transducer array. As is the case with sector scanning, each acoustic scan line is steered, so that no two scan lines are parallel to each other. As is also the case with sector scanning, each scan line, when projected or extended, has a common vertex, but unlike sector scanning, this common vertex need not lie on or near a line connecting the individual transducer elements or face of the transducer array. The common vertex can be anywhere and need not be on a centerline normal to the array.

For applications in which ultrasound information is collected for B-mode imaging and either Doppler or color flow imaging that is effectively simultaneous, the variable vertex format can be utilized in combination with a conventional format to substantial benefit. An example is the use of the variable vertex format for B-mode imaging in combination with a steered linear format for color flow imaging. The enhanced near field or the variable vertex format permits the use of small foot print transducers for near field applications, while the steered linear format is highly effective for color flow imaging of the near-in blood vessels that often run parallel to the skin line. In particular, the artifactual changes in color that would ordinarily occur as a result of the changing angle of interrogation are eliminated.

The variable common vertex location may optimize the field of view for a particular transducer geometry. The only constraint is that the steering angle with respect to a normal to a line connecting the transducer elements may not be greater than the greatest permitted for a sector scan line for the same transducer geometry. This criterion is determined by an acceptable grating lobe amplitude. A conservative criterion which effectively suppresses grating lobes limits the steering angle $\theta_o$ as follows:

$$|\theta_0| \leq \sin^{-1}\left(\frac{\lambda}{d} - 1\right), d \geq \pi/2$$

where $\lambda$ is the transducer center-frequency wavelength and d is the element spacing This criterion keeps the center of any grating lobe at an angle of at least $-90°$ with respect to the previously mentioned normal. Greater steering angles can be used where the array elements have sufficient directivity. A gradual lowering of the center-frequency, increasing the wavelength, as the array is steered away from normal suppresses grating lobes so as to permit greater steering angles, too.

The scanning method of this invention is general and accommodates many array physical geometries. Scanning a planar, curved or general curvilinear array of transducer elements is enabled simply by forming independent acoustic scan lines at arbitrary points of origin on the face of the array steered to an arbitrary angle with respect to a normal to the array at the scan line origin. The acoustic lines preferably are selected to be spatially non-overlapping in the entire field of view to accommodate operation with multiple simultaneous acoustic beams for improved frame rate or simultaneous Doppler and image scanning. Shifting and steering of each active acoustic line is software-programmable to optimize the field of view for variations in transducer operating frequency or to respond dynamically to situation-dependent phenomena such as presence of obstructions in the field of view (ribs, for example).

The substantially common vertex of the preferred embodiment is a special case of this invention. More generally, this invention describes a method of scanning a planar, curved or general curvilinear array of transducers in which substantially each scan line originates from an arbitrary but different location on the transducer array and substantially each scan line might be steered to a different angle with respect to the normal to the array at the point of origin of the scan line.

DESCRIPTION OF THE PREFERRED EMBODIMENT

Figure 1:
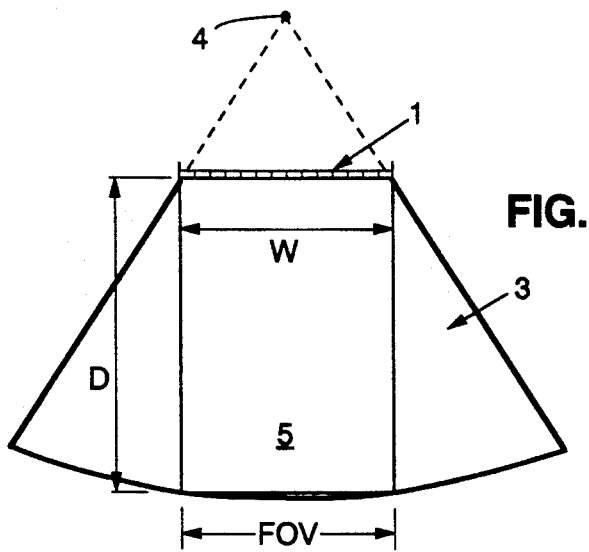
FIG. 1 is a view of the image plane for a linear scanning format with scan lines normal to the face of a planar linear transducer array with a variable vertex format superimposed upon it.

FIG. 1 illustrates the image plane of a rectangular linear scanning format from the planar linear transducer array 1. The scanned field of view 5 can be substantially expanded to a variable vertex format 3 of the invention by scanning a set of acoustic lines extending through a common vertex 4 behind the face of the transducer array.

Figure 2:
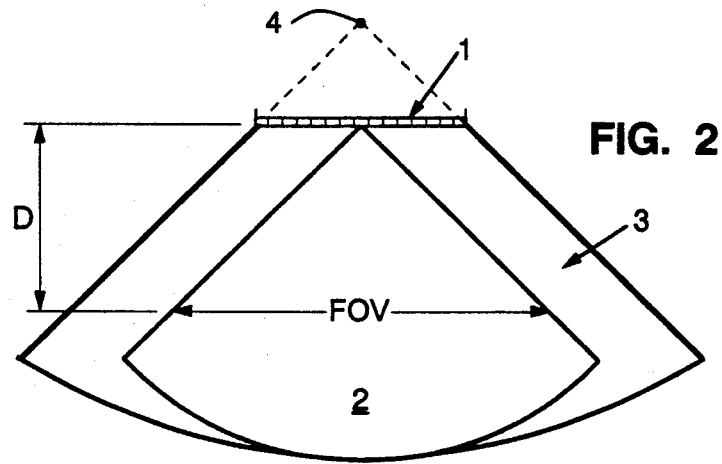
FIG. 2 is the image plane of a sector scanning format with the variable vertex format superimposed upon it.

FIG. 2 illustrates the image plane for a sector scanning format produced by transducer array 1. The typical sector field of view 2 can be expanded to the illustrated variable vertex format 3 by scanning acoustic lines derived from a common vertex 4 behind the face of the transducer array 1. The variable vertex format utilizes the entire array of transducer elements in the nearfield and substantially expands the entire field of view without significant loss of resolution anywhere within the typical sector field of view 2.

Figure 3:
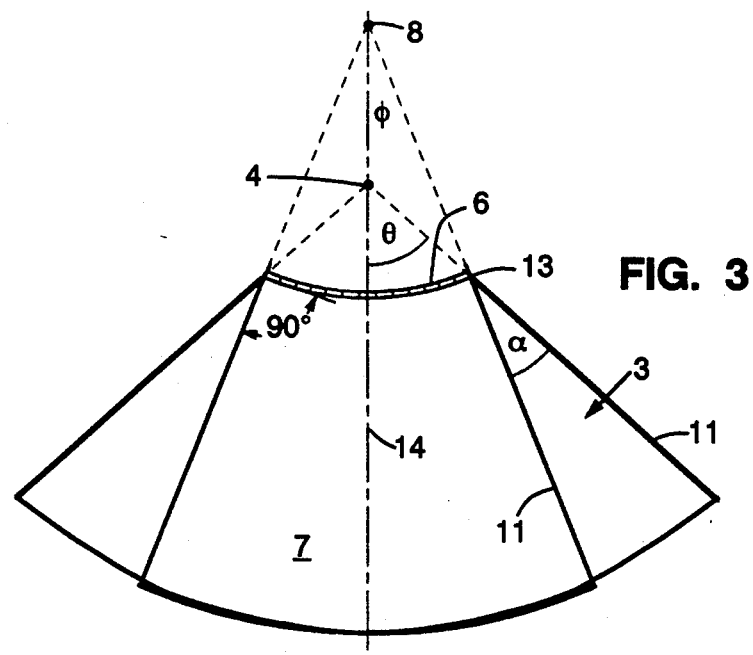
FIG. 3 illustrates the image plane formed by a curvilinear transducer array with a variable vertex format superimposed upon it.

FIG. 3 illustrates a curvilinear transducer array 6 and the field of view 7 obtained by multiple acoustic lines propagated normal to the face of the transducer array. Extensions of these normal acoustic lines pass through a common center of curvature 8. The field of view for the curvilinear transducer array can be expanded into the variable vertex format 3 by a set of acoustic lines propagated at varying angles to the face of the curvilinear array, extensions of which all pass through common vertex 4, where that common vertex is preferably between the center of curvature 8 and the face of the array.

For a curvilinear array, each acoustic scan line 11 originates from a different arbitrary point 13 on the face of the curvilinear array. These points of origin can be described by the angle $\phi$, the center of curvature 8 and the centerline of the transducer array 14. Alternately, in the variable vertex format each origin 13 for the ultrasound lines can be described by the angle $\theta$, the common variable vertex 4 and the centerline 14 connecting variable vertex 4 to the center of curvature 8 of the array. As shown in FIG. 3, each acoustic line for the variable vertex format is steered at the angle $\alpha$ with respect to the normal to the face of the curvilinear array. In FIG. 3 the center of curvature 8 is on the centerline 14 of the transducer array and the angle $\alpha$ equals the angle $\theta$ less the angle $\phi$. The delay equations for focused scanning with a curvilinear transducer array can be derived using these angular relationships and the location of the common vertex 4 relative to the radius of curvature 8 in a manner similar to the following translation of the planar linear array equation as at (6).

Figure 4:
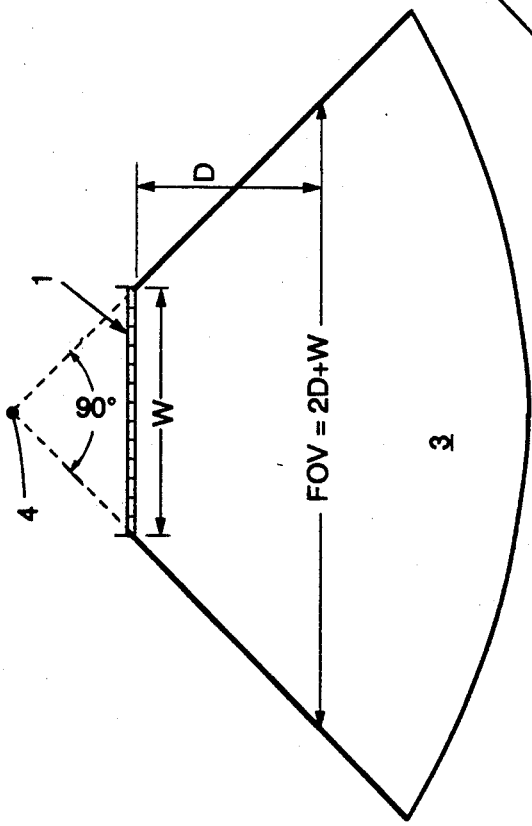
FIG. 4 illustrates the image plane of a variable vertex format illustrating its extended field of view at depth.

As is well known, the typical sector scan format has two major advantages when compared to the linear format. Namely, the sector has substantially increased field of view at the deeper scan depths, such as 10 cm. or greater when compared to the linear format, and the transducer used for sector scanning is physically smaller than that used for the linear scan format, typically by a factor of 3 or more. As is also well-known, a major disadvantage of the sector scan format is the extremely limited field of view at shallow scan depths, such as 1 cm. or less. One major improvement from the preferred embodiment of this invention is that a variable vertex scan format permits increased field of view at all scan depths, including shallow scan depths, by an amount up to and including the physical array width when compared to sector scanning as shown in FIG. 4 without substantial loss in resolution within the sector field of view 2 when compared to sector scanning.

Figure 5:
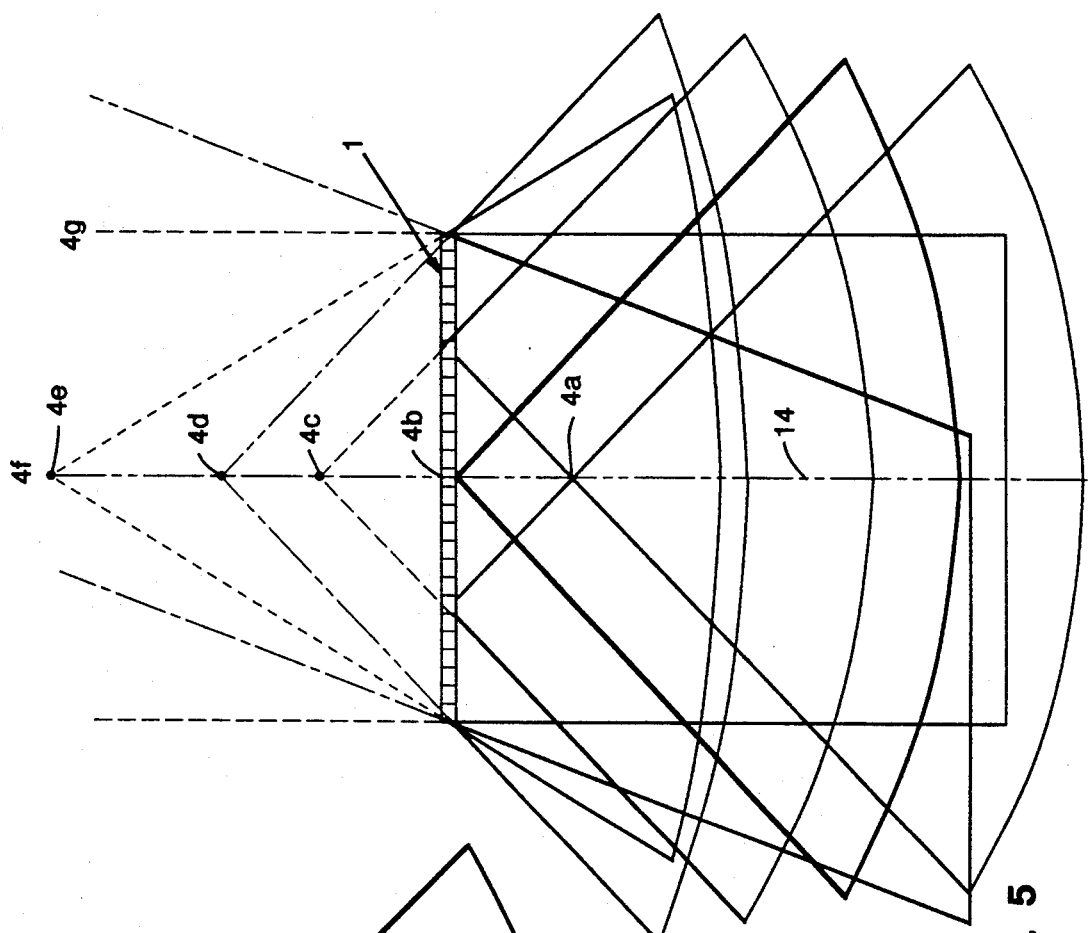
FIG. 5 illustrates a variable vertex format with a variety of locations for a common vertex.

The variable vertex scan and corresponding display format generally applies to linear or curvilinear arrays and is a generalization of the sector scan, except that the vertex may occur at a variable point as shown in FIG. 5 for several different placements of variable vertex 4a–4g. As the variable vertex approaches infinity 4f or 4g the format approaches a linear scanning format. As the variable vertex approaches the face of the transducer at 4b, the format approaches a sector format. The variable vertex may be in front of the transducer array as at 4a and at a location not on a normal line 14 through the center of the array as at 4g.

Figure 7:
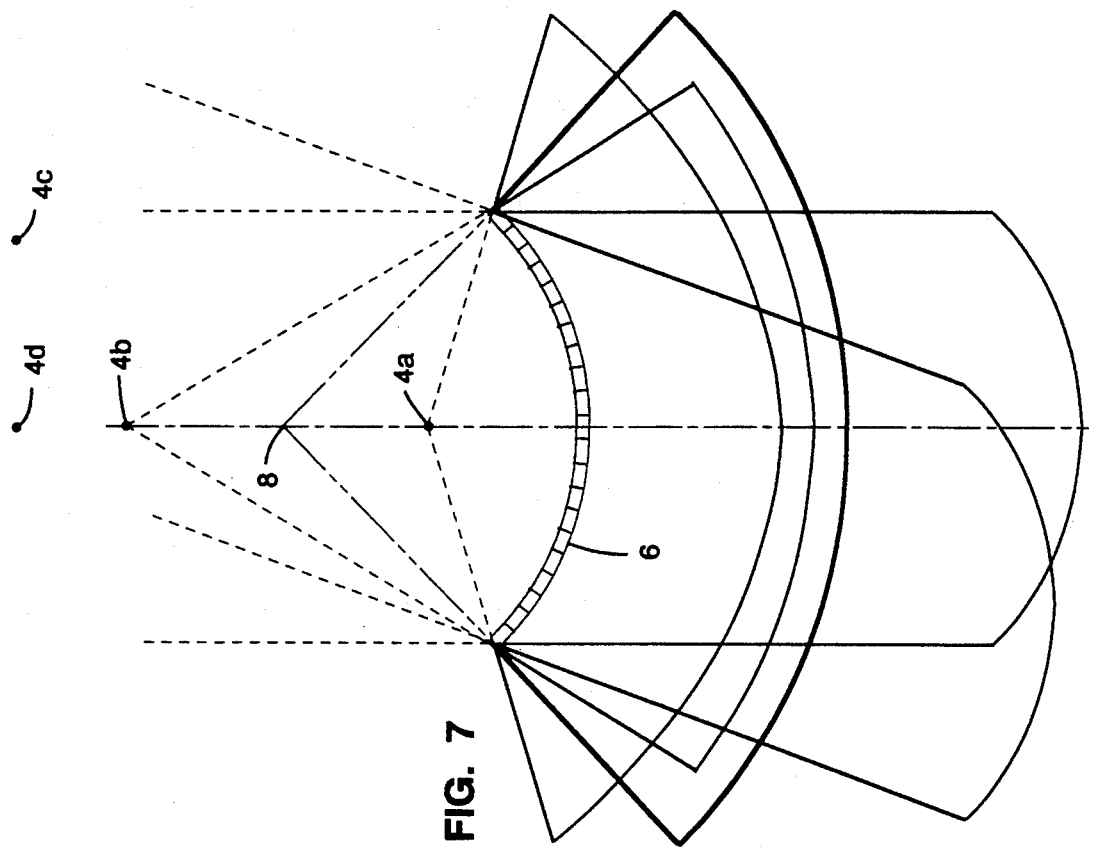
FIG. 7 illustrates a variable vertex format for a curvilinear transducer array with five different placements of a common vertex.
Figure 6:
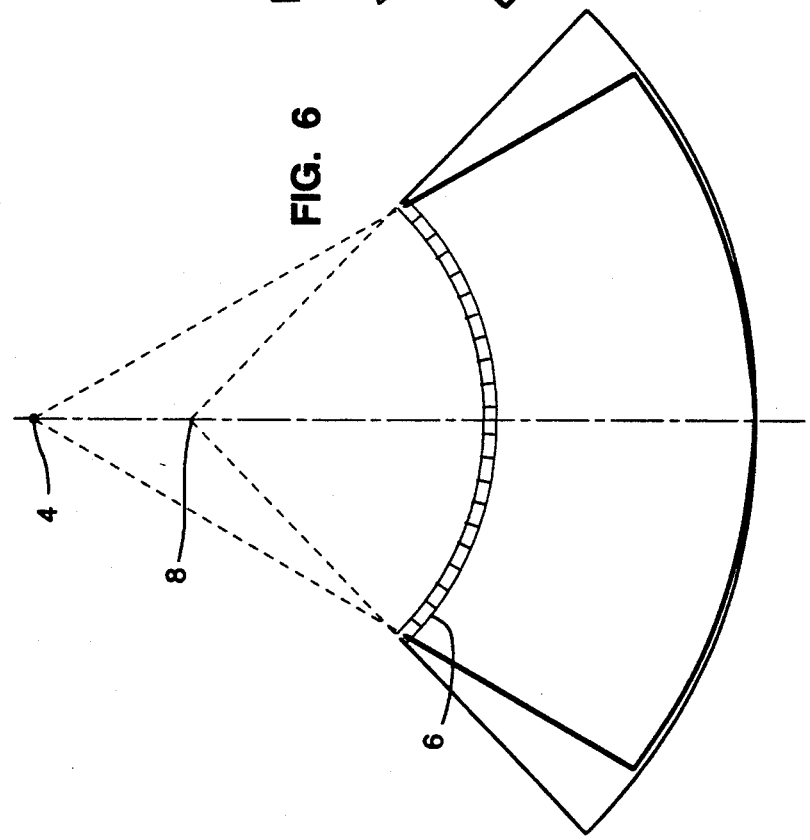
FIG. 6 illustrates a variable vertex format for a curvilinear transducer array with a common vertex at a radius greater than the radius of curvature.

Similarly, for curvilinear transducer arrays 6 the variable vertex 4 may be located at a radius behind the array that is greater than the radius of curvature 8 as shown in FIG. 6. So, too, can the variable vertex be placed at any location behind the array such as at 4a–4d shown in FIG. 7.

A principal objective of the described preferred embodiment of this invention is to define a scan and display format for an imaging system for which a common vertex 4 of all acoustic scan lines can be selectively positioned at any point within the scan plane. As illustrated for a planar array in FIG. 8, the variable vertex 4 is on a line normal to a line connecting all transducer elements of the physical aperture or face 12 of the array at a distance y behind the face of the array. However, the variable vertex need not lie on this line and may be placed in front of the physical aperture as well as behind it. The image format which results from the location shown in FIG. 8 benefits from an increased field of view at all depths and in particular near the physical aperture.

Figure 16:
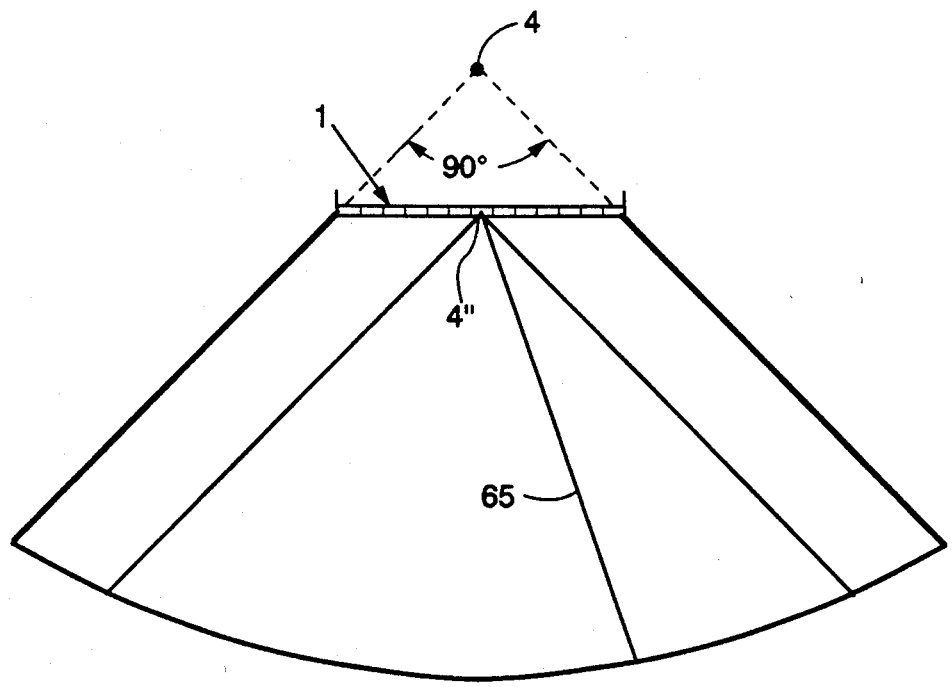
FIG. 16 illustrates variable vertex 2-D scanning in combination with sector continuous wave Doppler scan lines.
Figure 17:
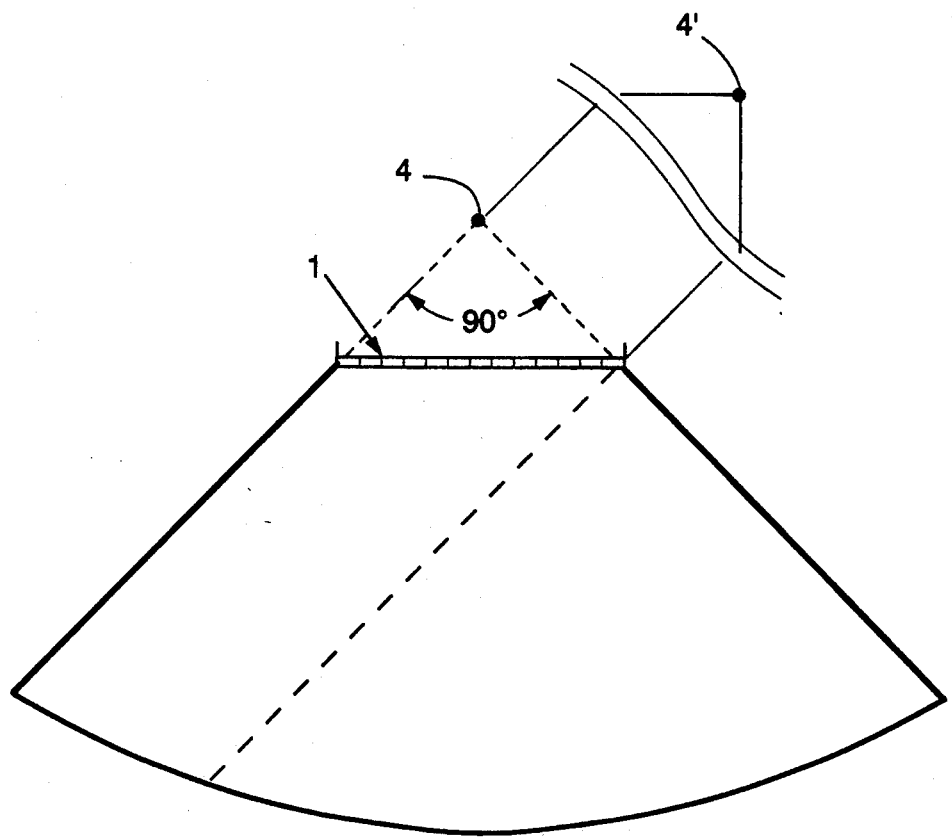
FIG. 17 illustrates variable vertex 2-D scanning in combination with nearly parallel color Doppler lines.

The format applies equally well to spectral Doppler and color flow Doppler scanning as well as to B-mode imaging. In particular, certain mixed modes enhance the utility of variable vertex scan and display format. Examples include: a variable vertex scan format in 2-D in combination with substantially parallel color flow scan lines, shown in FIG. 17 from a remote vertex 4'; multiple pulsed Doppler scan lines with variable vertices that are distinct from each other in combination with a 2-D image; or a continuous wave Doppler scan with lines 65 emanating from a variable vertex 4'' positioned at the center of the transducer, in combination with a 2-D scan format where the variable vertex 4 has been placed behind the transducer face as shown in FIG. 16.

Figure 23:
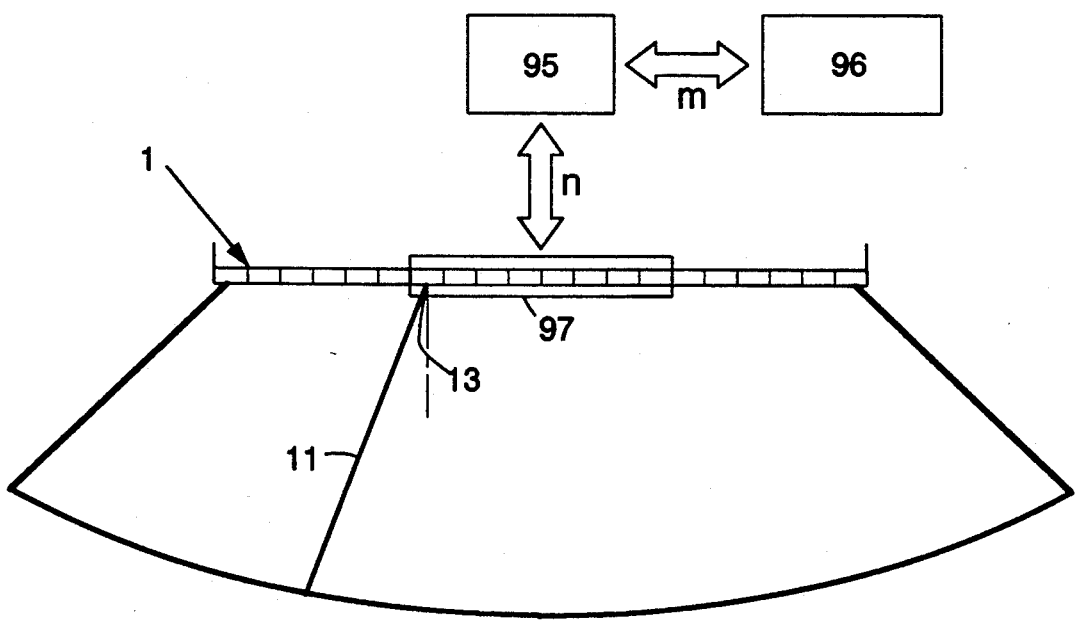
FIG. 23 schematically illustrates the invention applied to a multiplexed planar linear transducer array.

The scanning method of this invention applied to a multiplexed system is illustrated schematically in FIG. 23. There multiplexed sub-sets of m elements, such as 97, from the larger array 1 of n transducer elements are activated. The sub-sets 97 of active elements are selected by a multiplexer 95 from the larger group, n, and a system having m independent channels as at 96 controls beam propagation and processes the receive information. The multiplexer 95 may select sub-sets of m adjacent transducer elements or other groupings such as every other one of the n elements, for example.

Figure 8:
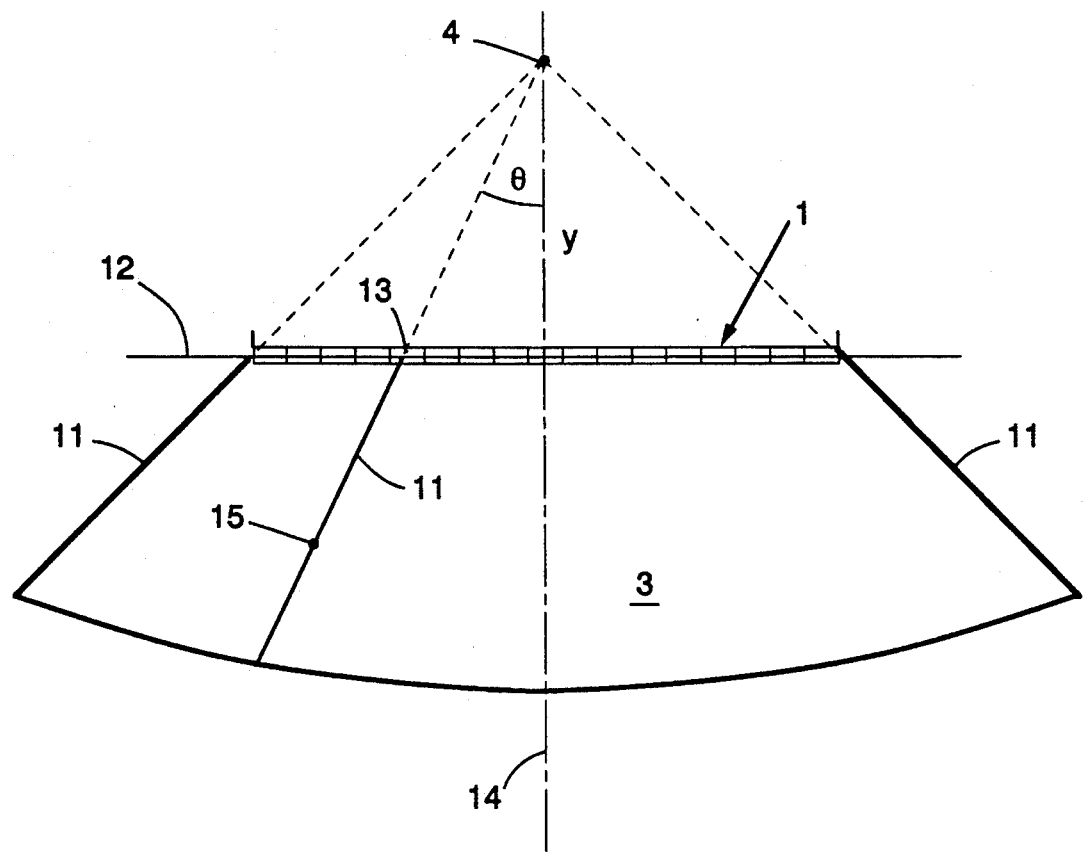
FIG. 8 illustrates the image plane of a variable vertex format showing a typical acoustic scan line in its extended field of view from a common vertex behind the face of the transducer array.

Included in the described embodiment of this invention is the method and means to select an origin 13, as shown in FIG. 8, and focal point 15 for a particular ultrasound beam such that the acoustic scan line 11 appears to emanate from the common vertex 4. The actual origin of an ultrasound beam for the planar array of FIG. 8 occurs on a line connecting the individual transducer elements at the point corresponding approximately to the center of mass of its apodization function. Equation (1) is used to manage the apodization function such that its center of mass is equivalent to or nearly equivalent to the intended origin 13 of the acoustic scan line 11. The origin 13 of the beam therefore can be controlled by smoothly shifting this center of mass. The shift required to place the beam origin 13 at or near the intersection 13 of a line connecting all elements of the transducer on the face 12 of the array with an acoustic scan line 11 which connects the variable vertex 4 to the focal point, as at 15, depends upon the spatial position of the variable vertex and the steering angle $\theta$.

Figure 11:
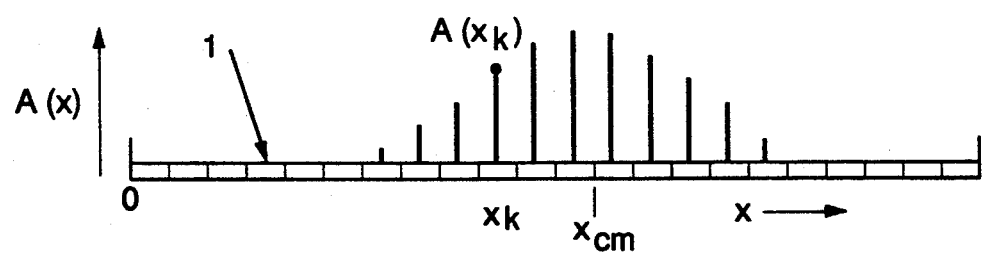
FIG. 11 illustrates a typical apodization function for an acoustic scan line.

By way of example, in FIG. 11 an ultrasound beam from the planar array of FIG. 8 originates from approximately the center of mass, $X_{cm}$ of its apodization function. The apodization function $A(X_k)$, may be described as the weighing given to the signal transmitted from, or received from, an element at position $X_k$. The center of mass for the apodization function is $$X_{cm} = \frac{\sum_{k=0}^{L} \int_0^{X_L} X \cdot A(X) \cdot \delta(X - X_k) \cdot dX}{\sum_{k=0}^{L} \int_0^{X_L} A(X) \cdot \delta(X - X_k) \cdot dX} \quad (1)$$

where $\delta(x)$ is the Dirac delta function and has the property that $$\int_{-\infty}^{\infty} f(X) \cdot \delta(X - X_k) \cdot dX = f(X_k)$$

Controlling the ultrasound beam origin is achieved by assigning the apodization values to each element of the physical transducer array in such a way that the center of mass $X_{cm}$ corresponds to the acoustic scan line origin 13. There is no requirement that $X_{cm}$ corresponds to an element position. In principle, the center of mass is computed for each acoustic scan line 11 and a unique apodization profile is generated for each scan line. In actual practice, only a limited set of profiles are required by taking the shift invariance property of the apodization profile into account. This means that, for example, one can cause the center of mass to shift by exactly one element spacing by simply shifting the assignment of each apodization value from the $k^{th}$ element to the $(k+1)^{th}$ element. This operation is easy to accomplish by means of control logic in combination with a microprocessor during the quiescent period between successive acoustic scan lines. Another unique set of apodization profiles is required to shift the center of mass by a fraction of an element spacing. Typically the position of the center of mass (and therefore the ultrasound beam origin) is controlled to within about one-quarter of a wavelength for foci close to the transducer array. For a typical sector-type transducer with half-wavelength spacing, this requirement corresponds to two unique families of apodization profiles. All other combinations required for each unique acoustic scan line are obtained by simple shift operations applied to one of these sets.

Figure 9:
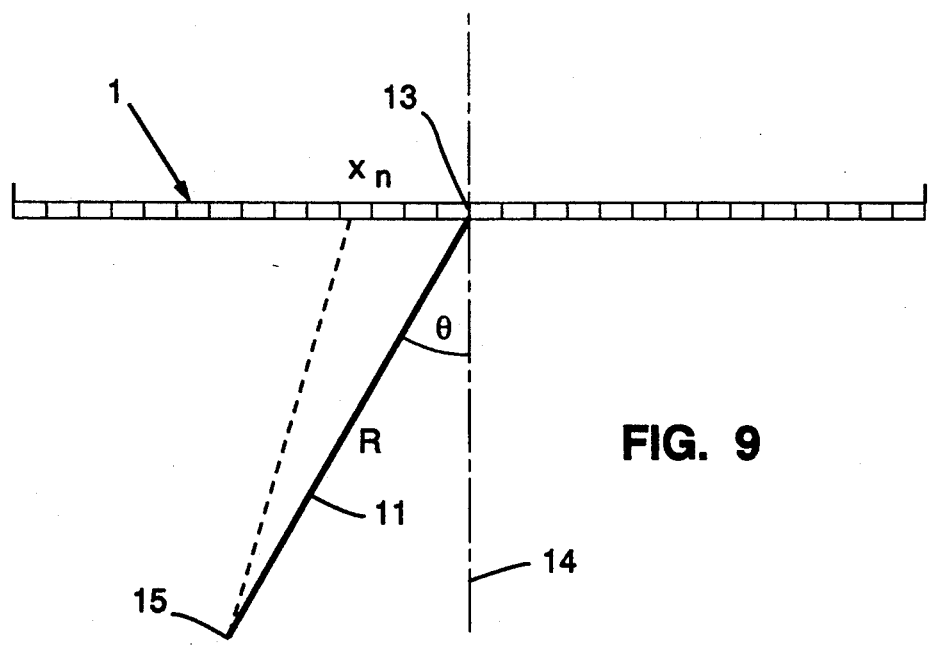
FIG. 9 is a schematic diagram from which delay equations are developed for the usual sector scan format.

For a sector scan format as shown in FIG. 9, the time delay which must be added to the n element, in order to have a focal point at range R, as at 15, along acoustic scan line 11 from the center of the transducer array and at an angle $\theta$ with respect to a reference line 14 is given as:

$$T_n(R, X_n, \theta) = \frac{1}{C_0} \{R - [R^2 + X_n^2 - 2RX_n\sin\theta]^{\frac{1}{2}}\} + T_{off} \quad (2)$$

where:

$T_n$ 32 the delay required at element position $X_n$ to achieve a focus at range R and steering angle $\theta$.

R = the range from the sector vertex or origin 13 to the focal point.

$X_n$ = the position of the $n^{th}$ element relative to the sector vertex or origin 13.

$\theta$ = the steering angle with respect to a reference line as shown in FIG. 9.

$T_{off}$ = a variable offset added to each delay in order to assure that the delay assigned to each element is positive. (Negative delay cannot be achieved.)

$C_0$ = the velocity of propagation in the body (typically 1.54 mm/usec).

This equation is well-known for sector imaging and is discussed, for example, in U.S. Pat. No. 4,140,022.

Figure 10:
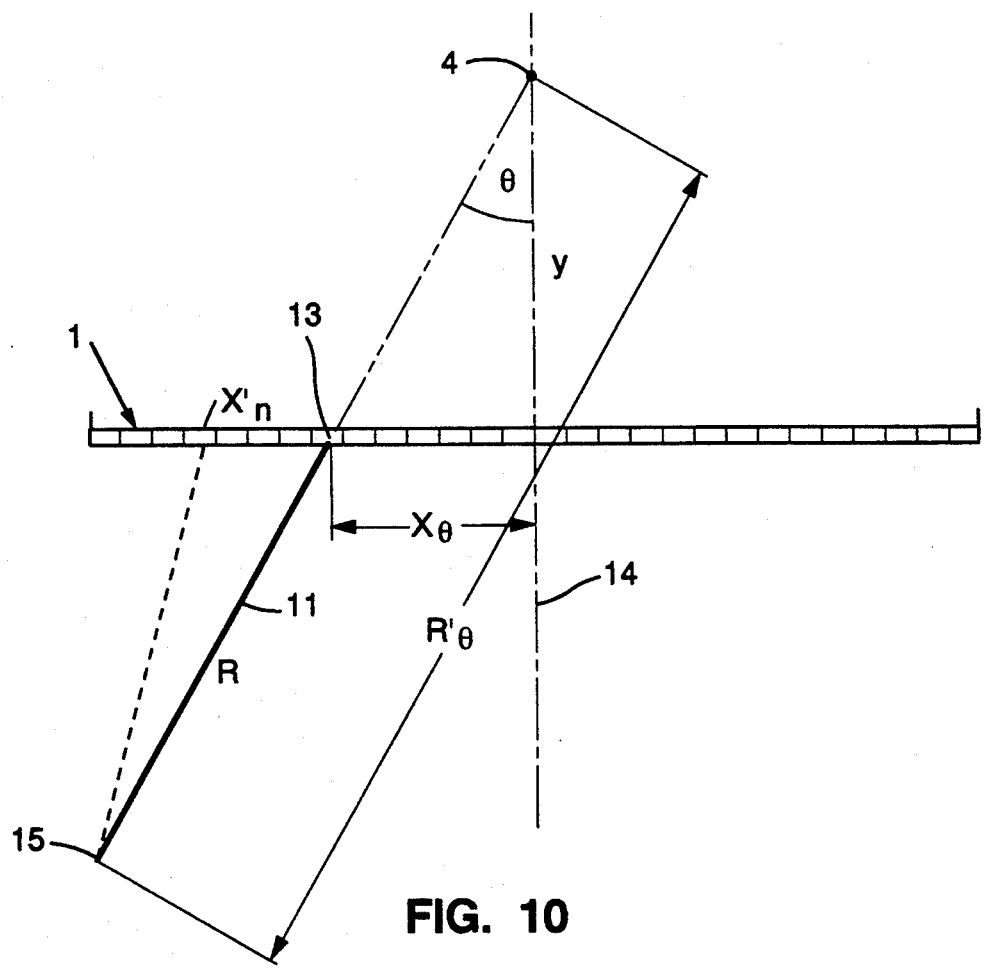
FIG. 10 is a schematic diagram from which delay transformation equations are developed for any arbitrary transducer element in a variable vertex format.

The time delay which must be added to the $n^{th}$ element in order to have a focal point at a range $R'_\theta$ from the variable vertex 4 and at angle $\theta$ with respect to the reference line 14 as shown in FIG. 10 for the variable vertex scan format is given by:

$$T_n(R'_\theta, X_n, \theta, y) = \frac{1}{C_0} \left\{ \left(R'_\theta - \frac{y}{\cos\theta}\right) - \left[\left(R'_\theta - \frac{y}{\cos\theta}\right)^2 + (X_n - y\tan\theta)^2 - 2\left(R'_\theta - \frac{y}{\cos\theta}\right) \cdot (X_n - y\tan\theta)\sin\theta\right]^{\frac{1}{2}} \right\} + T'_{off} \quad (3)$$

where $R'_{74}$ = the distance along a ray which is at an angle with respect to the reference line 14 (see FIG. 10) between the variable vertex and the focal point.

y = the offset along a normal to the physical array to the variable vertex.

$\theta$ = the steering angle with respect to the reference line as shown in FIG. 10.

$T'_{off}$ = an arbitrary variable offset added to each delay in order to assure that the delay added to each element is positive.

If one considers the substitutions $$R'_\theta = R + \frac{y}{\cos\theta} \quad (4)$$

$$X_\theta = y\tan\theta \quad (5)$$

then equation (3) becomes $$T_n(R, X'_n - X_\theta, \theta) = \qquad (6)$$

$$\frac{1}{C_0} \{R - [R^2 + (X'_n - X_\theta)^2 - 2R(X'_n - X_\theta)\sin\theta]^{\frac{1}{2}}\} + T_{off}$$

which has the same form as equation (2). Equation (6) shows how to compute the delay $T'_n$ appropriate for an element $X'_n$ which achieves focus 15 along acoustic scan line 11 at a distance $R'_{74}$ from the variable vertex 4 at an angle $\theta$ from the reference line 14. The collection of individual ultrasound lines used in a variable vertex scan format is calculated using equation (6) with each acoustic scan line having unique values for R, $X_{74}$, and $\theta$. The values R, $X_{74}$ and $\theta$ may be arbitrarily defined for each acoustic scan line.

Figure 21:
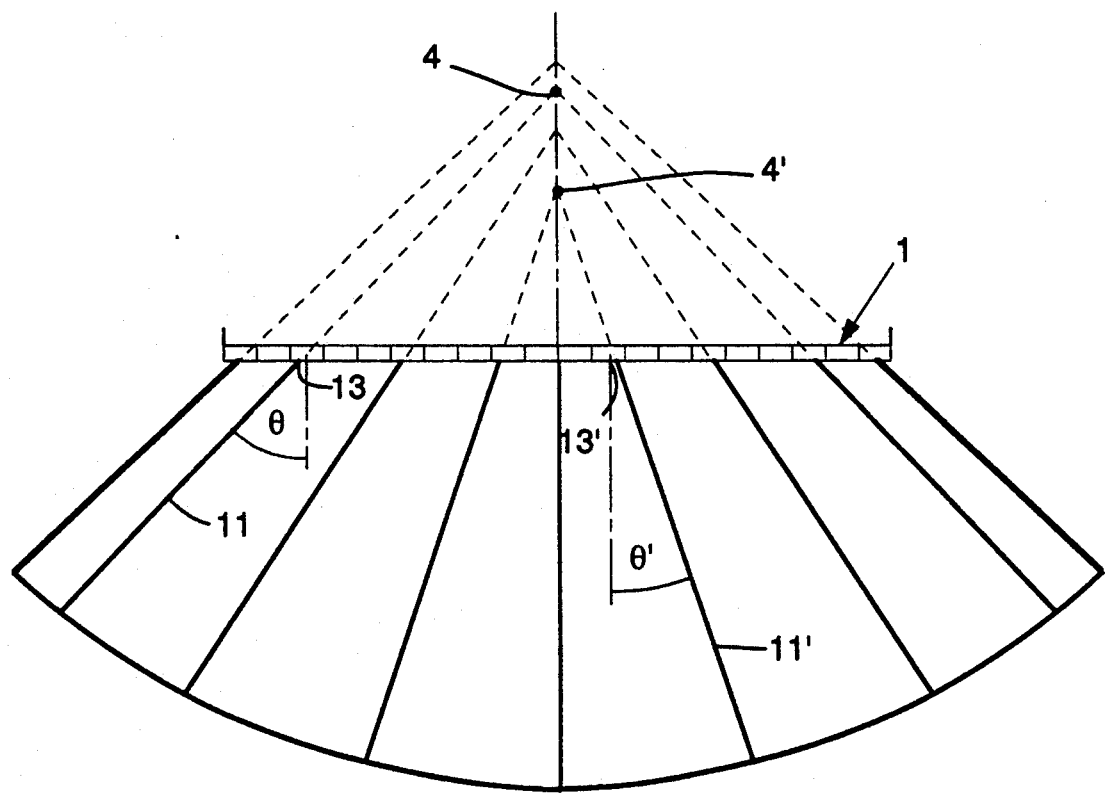
FIG. 21 schematically illustrates a scanning plane where the ultrasound scan lines do not have a common vertex.

Equation (6) discloses how to compute the delays for a planar array with a single fixed focal point along a ray at an angle $\theta$ with respect to a reference line. One such set of delays (one value per element position) is uniquely required for each acoustic scan line. In the more general case for this invention, each scan line originates at an arbitrary point on and at an arbitrary angle to the face of the array without a common vertex. Each individual scan line 11,11' originates at an arbitrary intersection or point such as 13,13' in FIG. 21 at the face of the transducer array 1 and is steered at an arbitrary angle $\theta, \theta'$ with respect to a normal to the array at its origin 13,13', respectively. As shown in FIG. 21, an extension of each of a symmetrical pair of scan lines may pass through a common vertex such as 4,4' for lines 11,11', respectively, along a normal line to the array. Thus, the loci of the variable vertex 4,4' for symmetrical pairs of lines may lie along that normal line rather than being a single common vertex as shown, for example, in FIG. 8. The scan lines also may have no common vertex at all.

Figure 22:
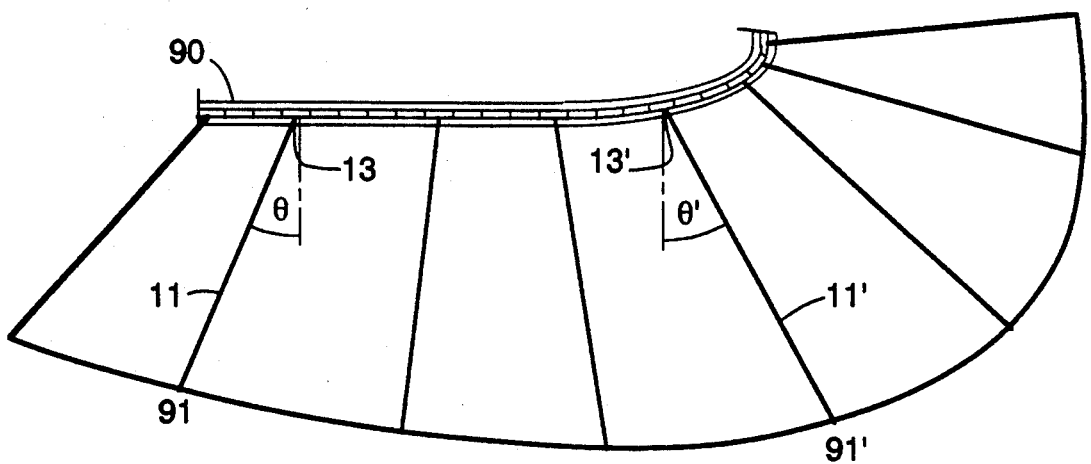
FIG. 22 schematically illustrates application of the invention to an arbitrarily shaped transducer array.

Similarly, the transducer array may be any generalized shape, such as at 90 in FIG. 22. Again, each scan line 11,11' originates at an arbitrary point 13,13' on the face of the array and at an angle $\theta, \theta$ with respect to a normal to the face of the array. As shown in FIG. 22, 13,13' is the vector position of the origin of the ultrasound lines and 91,91' is the vector position of a focal point along each line at the same or a different range from the transducer face. The apodization function for each line centers more or less about the arbitrary origin 13,13' at the face of the array. Time delays are calculated from the vector position of the $n^{th}$ element $X_n$, the vector position of the ultrasound line origin 13 ($O_k$) and the vector position of the focal point for the $k^{th}$ ultrasound line $F_k$. The equation below, in vector notation, is comparable to equation (6) for a fully arbitrary array and scan format $$T(\bar{X}_n, \bar{F}_k) = \frac{1}{C_0} \{|\bar{O}_k - \bar{F}_k| - |\bar{X}_n - \bar{F}_k|\} + T_{off}$$

For the preferred embodiment which is described, means to achieve dynamic focusing may be obtained by simply generalizing equation (6) to include a family of focal ranges, such as [$r_o, r_1 \cdots r_k$], rather than a fixed focal range, R. This constitutes a significantly large data set. That is, the amount of delay data required to achieve a fixed focus is given by

[Number of delay values]
= [N active transducer elements] · [M scan lines]
= $N \cdot M$ delay values In the case of mirror symmetry of the scan lines about a reference scan line, M is replaced by M/2 scan lines.

For a dynamically focused imaging system, with K focal ranges, this becomes (K·N·M) delay values. For a high performance ultrasound imaging system with 128 active transducer elements, this amounts to approximately $3 \cdot 10^5$ delay values. As a result, means to reduce the amount of high-speed RAM is a desired objective.

Data reduction can be achieved by means of a decomposition of the delay equation (6) into a reference (fixed) focus and a variable focus term. The approximation selected for the described embodiment is expressed as:

$$T_{An}(r,\theta,X_n,\rho,\theta_r) = T_n(\rho, X_n - X_{74}, \theta) + [T_n(r, X_n - X_{\theta r}, \theta_r) - T_n(\rho, X_n - X_{\theta r}, \theta_r)] \qquad 7$$

where:

$T_n(\rho, X_n - X_\theta, \theta)$ = The reference focus term
$[T_n(r, X_n - X_{\theta r}, \theta_r) - T_n(\rho, X_n - X_{\theta r}, \theta_r)]$ = The variable focus term $$T_n(r, X_n - X_\theta, \theta) = \qquad (8)$$

$$\frac{1}{C_0} \{r - [r^2 + (X_n - X_\theta)^2 - 2r(X_n - X_\theta)\sin\theta]^{\frac{1}{2}}\} + T_{off}$$

r = the desired (variable) focal range, i.e. represents one of the members of the set [$r_o, r_1 \ldots r_k$]
$\rho$ = a reference (fixed) focal range
$\theta$ = the steering angle
$\theta_r$ = a reference angle It can be shown that $T_{An}(r, \theta, X_n, \rho, \theta_r)$ approximates $T_n(r, X_n - X_\theta, \theta)$ to high accuracy provided that $\rho$ is selected to be approximately midway between the minimum and the maximum range for r (namely between $r_o$ and $r_k$); and $\theta_r$ is valid over an extent of about 25°. That is, a constant value of $\theta_r$ is valid to high accuracy for steering angles which are up to ±12.5° away from the specified reference value $\theta_r$. This leads to a reduction in the data set by a factor which is on the order of M·K/(M+K), which is at least an order of magnitude.

Figure 12:
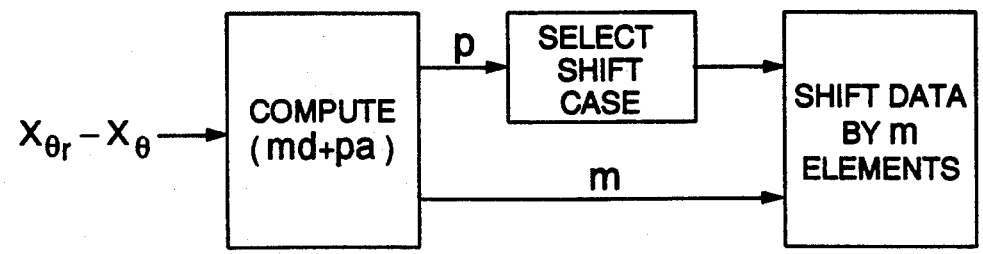
FIG. 12 schematically illustrates the selection and shifting of the delay data used for propagating the acoustic scan lines.

The variable focus term, which is $$T_{Vn}(r, X_n, \rho, \theta_r) = T_n(r, X_n - X_\theta, \theta_r) - T_n(\rho, X_n - X_{\theta r}, \theta_r) \qquad 9$$

has a very weak affect on steering. One can align the origin of the variable focussing term with that of the fixed focus term by recognizing that $$(X_n - X_\theta) - (X_n - X_{\theta r}) = m \cdot d + \epsilon \qquad 10$$

where
d = the inter-element distance
m = some integer
$\epsilon$ = a fractional remainder < d If $\epsilon \neq 0$, then the delay required to generate equation (9) from one scan line to another (in the range of $\theta$ for which the reference angle $\theta_r$ is valid) is generated by simply reassigning the delay value associated with the $k^{th}$ element to the $(k+m)^{th}$ element. Since, in general $\epsilon = 0$, then one must have additional sets of delay values corresponding to the variable focus term characterized by equation (9). If one defines the number of shift cases, p, such that $\epsilon \approx p \cdot a$, and a/2 is the greatest positional error which one is willing to accept, then one can rewrite equation (9) with the variable change $$(X_{74\,r} - X_\theta) \to m \cdot d + p \cdot a \qquad 11$$

where m and p are now control variables which are used as indices into the delay value data tables, and m is the number of single element delay value data positions by which the data must be shifted before it is applied. This is represented schematically in FIG. 12.

Figure 13:
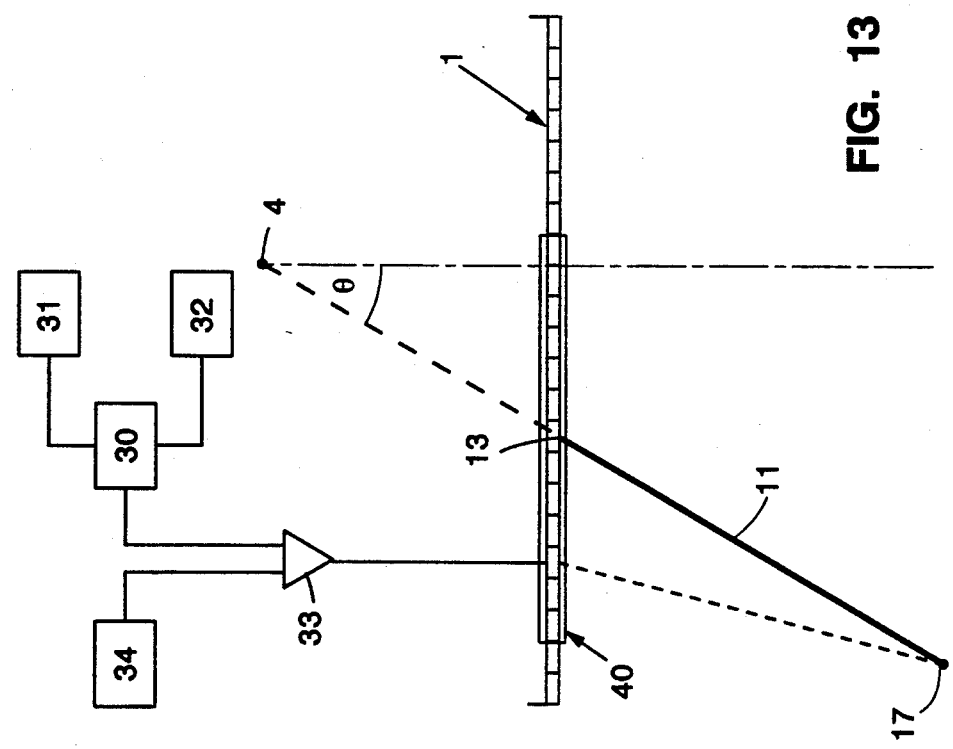
FIG. 13 schematically illustrates a variable vertex scan and requisite data necessary for transmit.

The foregoing shows how the delay calculations are generated and implemented to accommodate variable vertex imaging for a planar transducer array. Means by which the delay calculations are implemented to accommodate systems which employ heterodyning means in combination with coarsely quantized delay lines to achieve dynamic focussing as described in U.S. Pat. Nos. 4,140,022 and 4,550,607 follow in a straight-forward manner. For an active aperture 40, FIG. 13 demonstrates the generation and application of transmit delay information to the delay generator 30 by means of a shifting of the variable focus time delays 32 followed by summing with unshifted transmit reference focus time delays 31. This total time delay is then made available to the transmit drivers 33 as described in U.S. Pat. No. 4,550,607, for example. The center of mass of the apodization function is shifted by apodization generator 34.

Prudent apodization management requires that the active transmit aperture, as specified by the apodization function, increases about the center of mass as the selectable transmit focus gets further from the face of the transducer array. This is done to maintain a proper balance between quality of focus and depth of focus, as discussed in U.S. Pat. No. 4,550,607. Inevitably as the aperture grows, it will asymmetrically reach the end of the physical aperture. Under these conditions, one may either truncate that portion of the apodization function for which there is no physical aperture or choose to maintain the apodization shape, in either case shifting its center of mass toward the center of the physical aperture.

Figure 15:
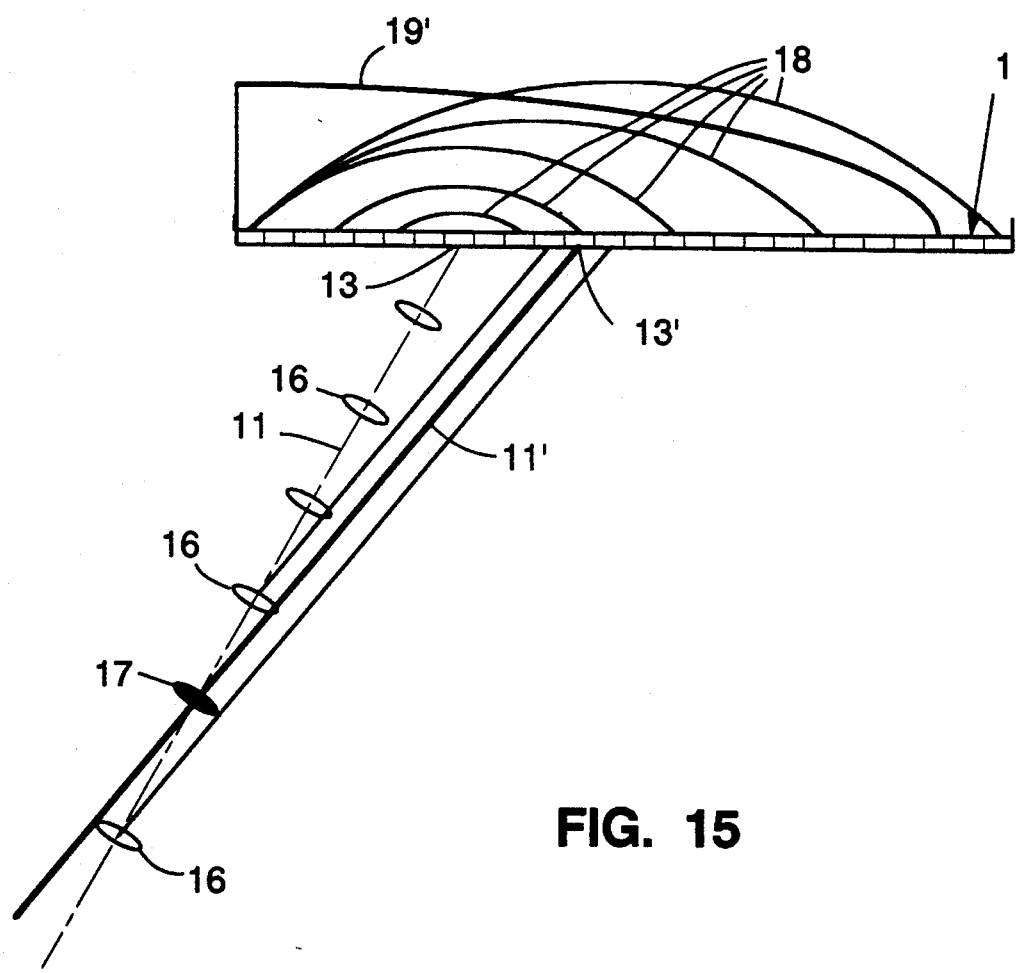
FIG. 15 illustrates end-aligned beamforming for a variable vertex format.

When the transmit apodization 19' in FIG. 15 becomes end-aligned, and its center of mass is shifted away from the desired beam origin, as at 13', the true beam axis 11' no longer aligns with the intended ultrasound scan line 11. An important feature of the scanning method of this invention is the ability to fire an acoustic scan line 11 through the physical end of the array. When a shallow transmit focus is selected, its active aperture is small with little opportunity to shift the beam origin away from its intended position. When a deep transmit focus is selected such as at 17, its active aperture is large and the beam origin may be shifted far away from its intended position 13, such as at 13'; however, with this large transmit aperture, the transmit ultrasound beam is relatively unfocussed close to the physical aperture where the displacement error is greatest. This poor focus minimizes the impact of the displacement errors, particularly if the correctly positioned receive focus is strong there. Conversely, near its focal point 17, the ultrasound beam axis and the acoustic scan line begin to intersect, and the displacement error diminishes, vanishing completely at the focal point. Beyond the transmit focal point 17, the ultrasound beam axis and scan line axis again diverge, but again, transmit defocussing minimizes the impact of the displacement errors as long as the receive focus is correctly positioned on the ultrasound scan line 11. The tracking of data along the scan line axis 11, and not along the misaligned ultrasound beam axis 11', is accomplished through the combination of dynamic receive apodization 18 and focussing 16.

Figure 14:
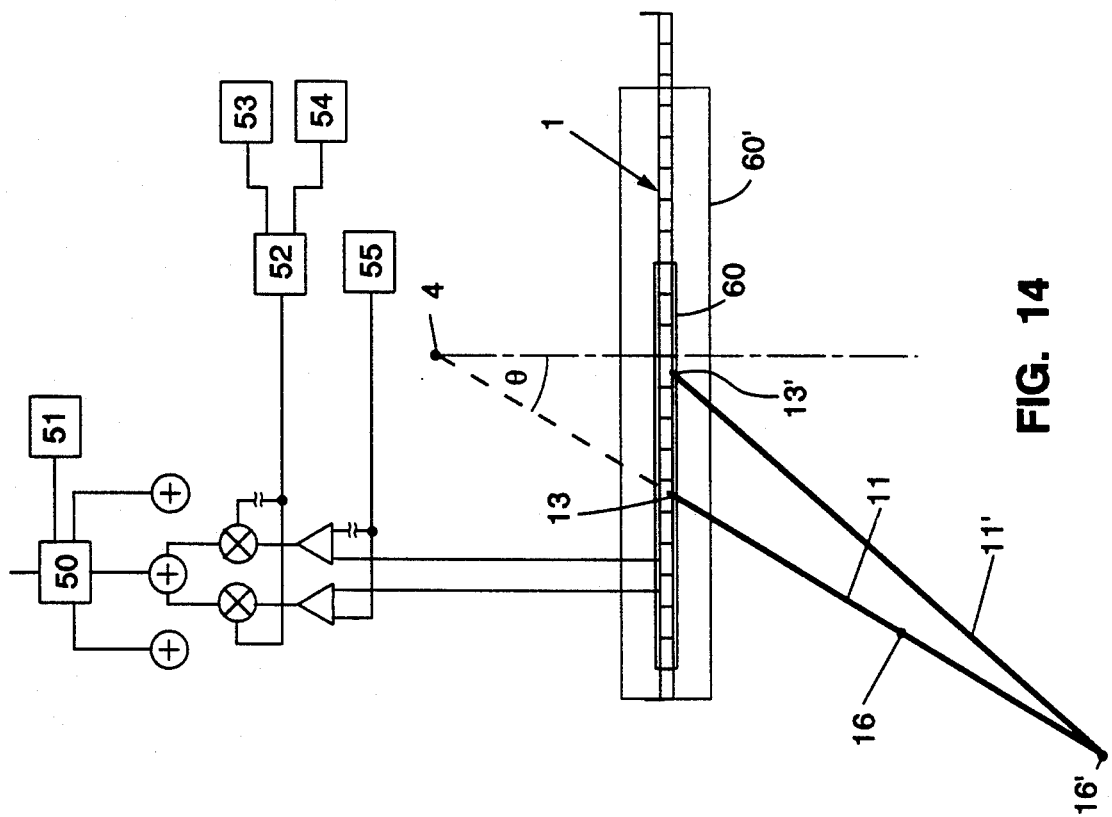
FIG. 14 illustrates a variable vertex scan and data necessary for receive with dynamic apodization and focussing.

During dynamic receive beamforming, the active receive aperture 60, as shown in FIG. 14, grows dynamically to 60' as the receive focus dynamically becomes farther from the physical transducer along the scan line 11 in such a manner as to keep the ratio of focal depth to active aperture width a constant to the greatest extent possible, as has been discussed in U.S. Pat. No. 4,550,607. As the receive aperture 60 grows dynamically to 60', it also becomes end-aligned, its center of mass is also shifted away from the desired beam origin, and the true beam axis 11' no longer aligns with the intended scan line axis 11. However, the receive focus 16 can always be placed on the ultrasound scan line axis 11. As the dynamic receive beamformer continually switches from one focus 16 to the next 16', it accurately tracks the information along the desired acoustic scan line 11.

A unique set of ideal time delay data is calculated at the receive reference focus for all elements and for all scan lines in a manner similar to that done for the transmit steering time delays. These ideal time delays can be decomposed into coarse and fine time delays applied at summing means 50 as described in U.S. Pat. Nos. 4,550,607 or 4,140,022.

The fine time delays may then be converted into phase as shown, for example, in U.S. Pat. Nos. 4,550,607 or 4,140,022. These delays are decomposed into a reference and variable focus phase and are made available to the receiver phase generator 52 in FIG. 14 which sums the reference component phases 53 with the shifted variable focussing component phases 54 to generate the composite receiver phase values. The receiver phase values are then used to select the phase of the mixer signals. The active receive aperture is controlled by the receive apodization generator 55.

Figure 18:
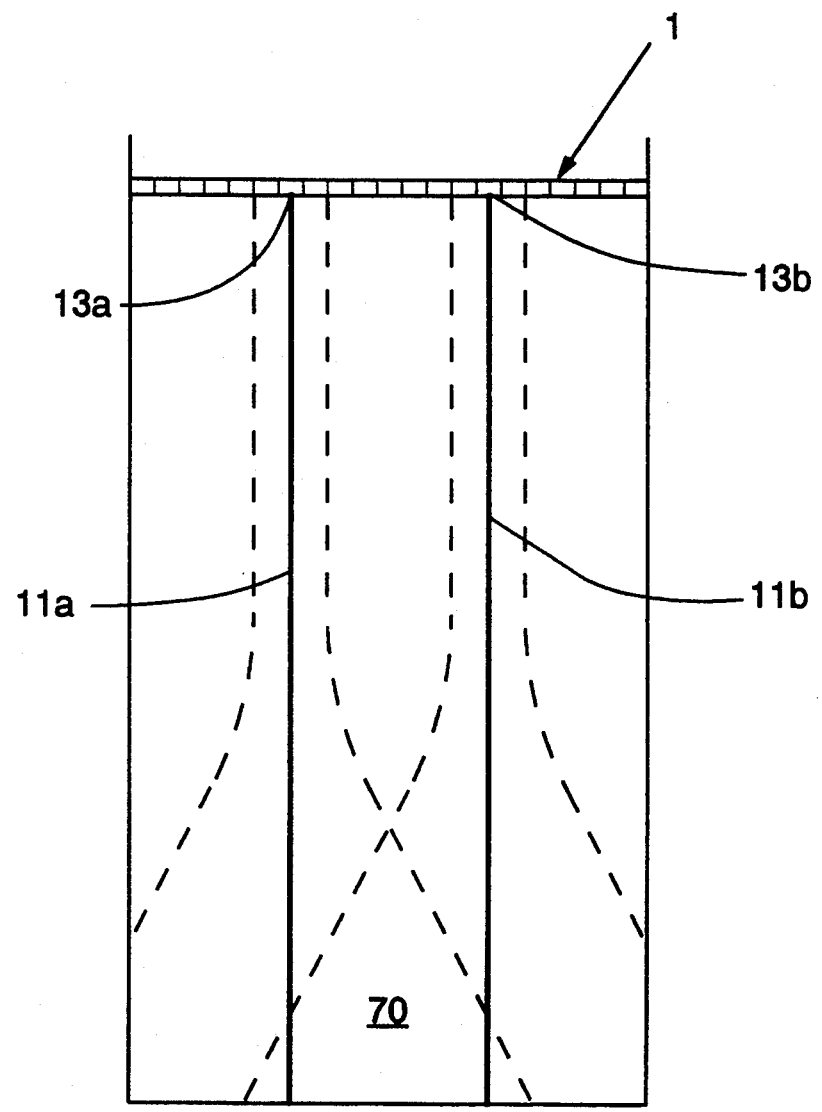
FIG. 18 illustrates the scanning plane for a linear scanning format for simultaneous propagation and receipt of echoes from two ultrasound beams.
Figure 19:
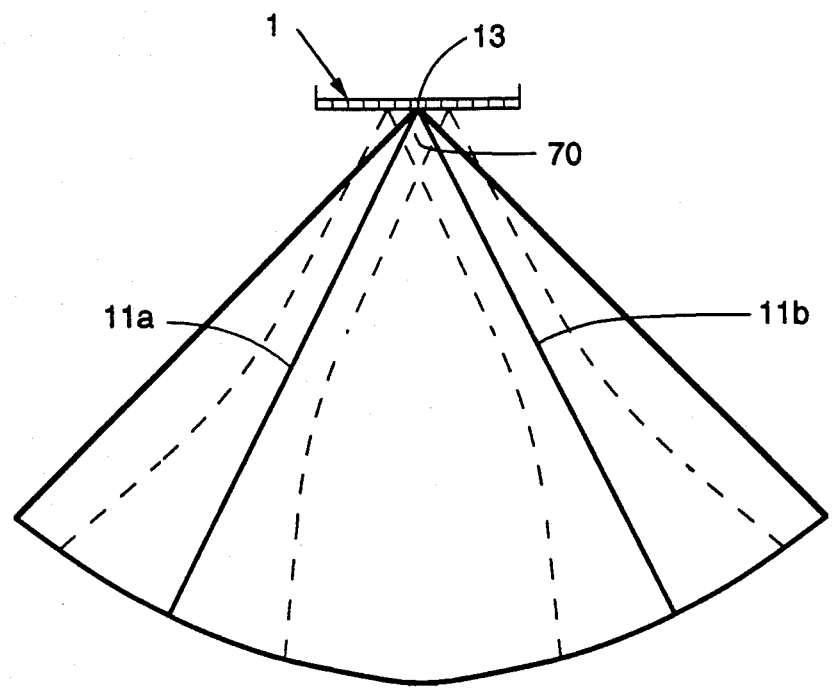
FIG. 19 illustrates the scanning plane for a planar sector scanning format for simultaneous propagation and receipt of echoes from two ultrasound beams.

Using phased array imaging systems, it is possible to activate, in transmit and receive, two or more beams substantially simultaneously from the same aperture 1 as shown in FIGS. 18 and 19. Simultaneous means that more than one pulse is in flight directed at possibly different spatial locations at any one time while scanning. This may be done with straight-forward modifications to systems which have previously been disclosed, as in, for example, U.S. Pat. No. 4,550,607. However, one significant problem with such systems is that multiple pulses or multiple beams along scan lines 11a, 11b tend to overlap as at 70 and interfere substantially away from the transmit focus in a planar linear format, as shown in FIG. 18 and especially in the near field, close to the transducer as shown in FIG. 19 for a typical sector scan.

Figure 20:
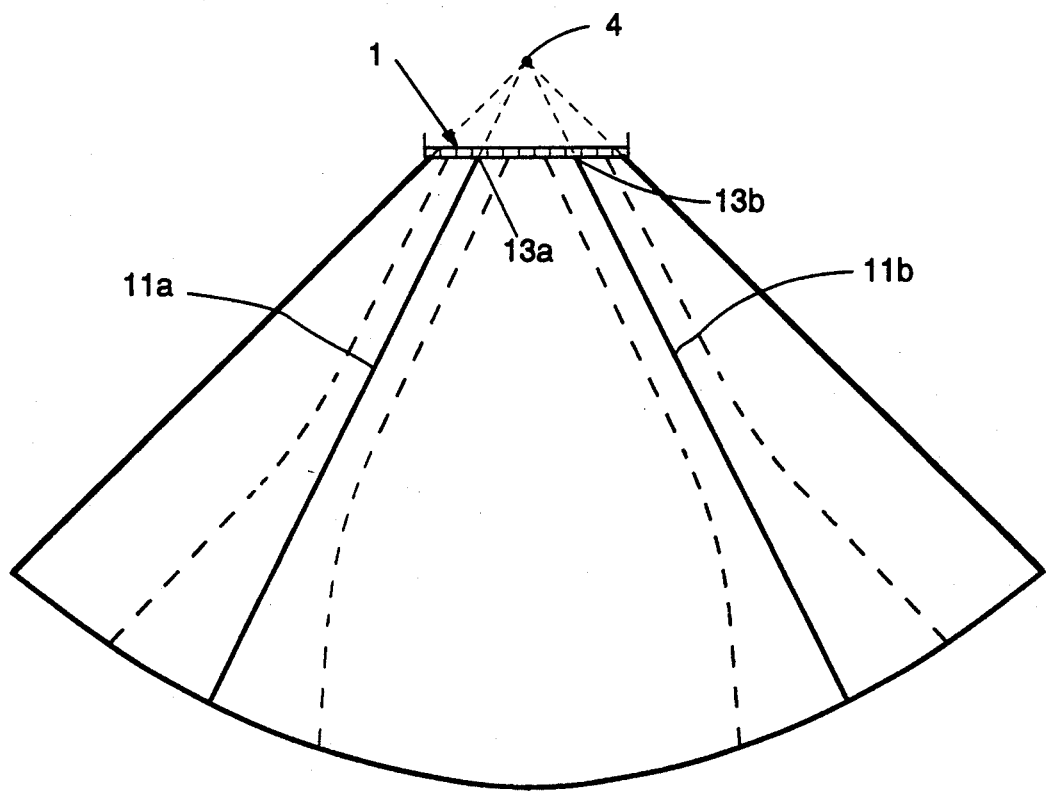
FIG. 20 illustrates the scanning plane for a variable vertex scanning format for simultaneous propagation and receipt of echoes from two ultrasound beams.

One major advantage of the variable vertex scanning format is the ability to separate multiple beams much more effectively, even if propagated simultaneously, because the ultrasound scan lines 11a, 11b are well-separated throughout the field of view 3 as shown in FIG. 20. Comparing FIGS. 18 and 19 with FIG. 20, it is apparent that the region of interference 70 is reduced or eliminated in FIG. 20 because of the separated origins 13a, 13b in the near field and because the scan lines 11a, 11b diverge in the far field. The active apertures for the two beams are substantially less overlapping rather than fully overlapping, as in a normal sector scan, even though the effective aperture for each beam is not reduced in extent. The intrinsic spatial separation of beams (including the near field) of the variable vertex format, in combination with dynamic apodization and dynamic focussing, effectively optimizes performance in multiple beam operation.

We claim:

1. A method for scanning an array of individual transducer elements for obtaining image, velocity or various data from a section of a body comprising the steps of
propagating acoustic pressure waves into the body from at least one active transmit aperture of individual transducer elements,
receiving acoustic echoes on a set of acoustic lines the centers of which are spatially non-overlapping, including the step of steering the angle of each acoustic line relative to the array, using for each line a variable active aperture of individual transducer elements which selectively includes only some or all elements of the array,
so that an extension of the acoustic line in space beyond its origin at the array passes through a substantially common vertex which is not located on the transducer array.

2. The method of claim 1 wherein said common vertex is located a selectable distance in space behind the transducer array so as to provide a selectable extended field-of-view of said body.

3. The method of claim 1 further including the step during reception of dynamically focussing along each acoustic line.

4. The method of claim 1 further including the step during reception of dynamically adjusting the size or center of the aperture of active transducer elements of the array.

5. The method of claim 4 wherein the shape of apodization is dynamically varied during reception along each scan line.

6. The method of claim 1 wherein said pressure waves are propagated and echoes are received simultaneously on more than one of said acoustic lines.

7. The method of claim 1 wherein the active transmit aperture of individual transducer elements is selectively variable to include only some or all elements of the array.

8. The method of claim 1 wherein the number of individual transducer elements in the active transmit aperture for propagating said pressure waves may differ from the number of elements in the active aperture which receives the acoustic echoes at each depth in the field-of-view.

9. The method of claim 1 wherein the set of acoustic lines includes sub-sets of acoustic lines generated by and received upon an active number of m individual transducer elements corresponding to available signal processing channels which are addressed by multiplexing from a larger number of n individually addressable transducer elements in the transducer array.

10. The method of claim 9 wherein each sub-set of acoustic lines has a common vertex different from the common vertex of each other sub-set of acoustic lines.

11. The method of claim 1 wherein pressure waves optimized for deriving Doppler information and pressure waves optimized for deriving B-mode image information are substantially simultaneously propagated from and echoes are received on more than one of said acoustic lines by the same transducer array.

12. The method of claim 11 wherein the Doppler waves are propagated at a frequency different from the frequency of the B-mode image waves.

13. The method of claim 11 wherein the Doppler waves are propagated in a direction different from the B-mode image waves in a linear scanning format.

14. A method for scanning an array of individual transducer elements for obtaining image, velocity or variance data from a section of a body comprising the steps of
propagating acoustic pressure waves into the body from at least one active transmit aperture of individual transducer elements,
receiving acoustic echoes on a set of acoustic lines the centers of which are spatially non-overlapping using for each line a variable active aperture of individual transducer elements which selectively includes only some or all elements of the array,
shifting on transmission or receive each acoustic line to originate from an arbitrary origin relative to the center of the face of said transducer array, and steering on transmission or receive each acoustic line at an arbitrary angle relative to the face of the array.

15. The method of claim 14 wherein the active transmit aperture of individual transducer elements is selectively variable to include only some or all elements of the array.

16. A method for scanning an array of individual transducer elements for obtaining an image of a section of a body and for obtaining velocity or variance information from that section of the body comprising the steps of
propagating first acoustic pressure waves at a first frequency for deriving image information and receiving acoustic echoes on a first set of acoustic image lines the centers of which are spatially non-overlapping,
steering the angle of each active acoustic image line relative to the array so that an extension of the line in space passes through a substantially common vertex, and
propagating second acoustic pressure waves at a frequency different from that of the first acoustic pressure waves for deriving velocity or variance estimates from Doppler-shifted echoes received from those second pressure waves on a separate second set of acoustic lines each of which may be independent from said acoustic image lines.

17. The method of claim 16 wherein the second acoustic pressure waves are propagated in a direction different from the image waves.

18. Apparatus for obtaining image, velocity or variance data from a section of a body on a set of acoustic lines scanned along a transducer array with each acoustic line originating on the array at an arbitrary origin relative to the center of the face of the array, comprising
an array of individual transducer elements adapted to be placed against the body,
means for propagating acoustic pressure waves into the body from at least one active transmit aperture of individual transducer elements in the array,
means for receiving acoustic echoes on a set of acoustic lines the centers of which are spatially non-overlapping including means for forming a variable active aperture of individual transducer elements which selectively includes only some or all elements of the array, means for shifting substantially all acoustic lines to originate from an arbitrary origin relative to the center of the face of said transducer array within the active aperture.

and means for electronically steering substantially all acoustic lines at an arbitrary angle relative to the face of the array.

19. The apparatus of claim 18 wherein the means for forming the active transmit aperture of individual transducer elements is selectively variable to include only some or all elements of the array.

20. The apparatus of claim 18 wherein the number of individual transducer elements in the active transmit aperture for propagating said pressure waves differs from the number of elements in the active aperture which receives the acoustic echoes at each depth in the field-of-view.

21. The apparatus of claim 19 wherein the array of individual transducer elements has a generalized and arbitrary shape.

* * * * *

UNITED STATES PATENT AND TRADEMARK OFFICE
CERTIFICATE OF CORRECTION

PATENT NO. : 5,148,810  
DATED : September 22, 1992  
INVENTOR(S) : Samuel H. Maslak et al Page 1 of 3

It is certified that error appears in the above-indentified patent and that said Letters Patent is hereby corrected as shown below:

IN THE DRAWINGS

In Fig. 15, the second 16 from the transducer face should be --16'--

Col. 8, line 5; "n element" should read -- $n^{th}$ element --

Col. 8, line 16; "$T_n 32$" should read -- $T_n =$ --

Col. 8, lines 38-47; equation (3) should read --

$$T'_n(R'_o, X'_n, \theta, y) = \frac{1}{c_0}\left\{\left(R'_o - \frac{y}{\cos\theta}\right) - \left[\left(R'_o - \frac{y}{\cos\theta}\right)^2 + (X'_n - y\tan\theta)^2 - 2\left(R'_o - \frac{y}{\cos\theta}\right)\cdot(X'_n - y\tan\theta)\sin\theta\right]^{\frac{1}{2}}\right\} + T'_{off}$$

Col. 8, line 51; "$R'_{74}$" should read -- $R'_\theta$ --

Col. 8, line 51; after the word "angle" insert -- $\theta$ --

Col. 9, lines 1-4; equation (6) should read --

$$T'_n(R, X'_n - X_o, \theta) = \frac{1}{c_0}\left\{R - \left[R^2 + (X'_n - X_o)^2 - 2R(X'_n - X_o)\sin\theta\right]^{\frac{1}{2}}\right\} + T'_{off}$$

UNITED STATES PATENT AND TRADEMARK OFFICE
CERTIFICATE OF CORRECTION

PATENT NO. : 5,148,810
DATED : September 22, 1992
INVENTOR(S) : Samuel H. Maslak et al It is certified that error appears in the above-indentified patent and that said Letters Patent is hereby corrected as shown below:

Col. 9, line 10; "$R'_{74}$" should read -- $R'_\theta$ --

Col. 9, lines 14 and 15; "$X_{74}$" should read -- $X_\theta$ --

Col. 9, line 41; "$\theta,\theta$" should read -- $\theta,\theta'$ --

Col. 10, lines 19,49,54; equations 7,9 and 10 missing parentheses around the equation numbers Col. 10, line 48; equation (9) should read --

$$T_{vn}(r, X_n, \varrho, \theta_r) = T_n(r, X_n - X_{\theta_r}, \theta_r) - T_n(\varrho, X_n - X_{\theta_r}, \theta_r)$$

Col. 10, line 60; "$\epsilon \neq 0$" should be -- $\epsilon = 0$ --

Col. 10, line 65; "$\epsilon = 0$" should be -- $\epsilon \neq 0$ --

Col. 11, line 4; equation 11 missing parentheses around the equation number

Col. 11, line 4; equation (11) should read --

$$(X_{\theta_r} - X_\theta) \rightarrow m \cdot d + p \cdot a$$

UNITED STATES PATENT AND TRADEMARK OFFICE
CERTIFICATE OF CORRECTION

PATENT NO. : 5,148,810

DATED : September 22, 1992

INVENTOR(S) : Samuel H. Maslak et al

It is certified that error appears in the above-indentified patent and that said Letters Patent is hereby corrected as shown below:

Col. 13, line 9; "various" should be -- variance --

Col. 16, line 9; change "19" to -- 18 --

Signed and Sealed this

Nineteenth Day of April, 1994

Attest:

BRUCE LEHMAN

*Attesting Officer*     *Commissioner of Patents and Trademarks*